United States Patent
Bernard et al.

(10) Patent No.: US 10,032,294 B2
(45) Date of Patent: Jul. 24, 2018

(54) METHOD AND SYSTEM FOR OBTAINING LOW DOSE TOMOSYNTHESIS AND MATERIAL DECOMPOSITION IMAGES

(71) Applicant: GENERAL ELECTRIC COMPANY, Schenectady, NY (US)

(72) Inventors: Sylvain Bernard, Buc (FR); Razvan Gabriel Iordache, Buc (FR); Serge Louis Wilfrid Muller, Buc (FR); Giovanni John Jacques Palma, Buc (FR); Ann-Katherine Carton, Buc (FR); Pablo Milioni de Carvalho, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 86 days.

(21) Appl. No.: 14/978,460

(22) Filed: Dec. 22, 2015

(65) Prior Publication Data
US 2016/0189376 A1  Jun. 30, 2016

(30) Foreign Application Priority Data
Dec. 24, 2014  (GB) .................................. 1423174.0

(51) Int. Cl.
G06T 11/00 (2006.01)
A61B 6/02 (2006.01)
A61B 6/00 (2006.01)

(52) U.S. Cl.
CPC ............ *G06T 11/006* (2013.01); *A61B 6/025* (2013.01); *A61B 6/481* (2013.01); *A61B 6/482* (2013.01);
(Continued)

(58) Field of Classification Search
CPC . G06T 2211/408; G06T 7/0012; G06T 15/08; G01T 1/1603; H04N 5/32
See application file for complete search history.

(56) References Cited

U.S. PATENT DOCUMENTS 5,485,500 A *  1/1996  Baba .................. H04N 5/32
                                    348/E5.086
6,542,770 B2 *  4/2003  Zylka .................. A61B 6/12
                                    600/424
(Continued)

FOREIGN PATENT DOCUMENTS

EP    2230641 A1 *  9/2010 .......... G06K 9/00208
WO    2012122399 A1   9/2012

OTHER PUBLICATIONS

Combined Search and Exam Report for corresponding GB Appln. No. 1423174.0, dated Jun. 12, 2015, 6 pages.

*Primary Examiner* — Iman K Kholdebarin
*Assistant Examiner* — Mai Tran

(57) ABSTRACT

Method and system for obtaining tomosynthesis and material decomposition images of an object of interest using a system comprising an x-ray source facing a detector. The method comprises generating a 2D material decomposition image of an object of interest from at least two sets of acquisitions. Each set is performed at a different energy spectrum and comprises at least one projection image or a plurality of projection images acquired at different x-ray source angulation positions, and the 2D material decomposition image can be generated for a predetermined orientation selected from one of said different x-ray source angulation positions or from a virtual orientation. At least one of the plurality of 3D volume portion images and/or the 2D contrast enhanced material decomposition image are displayed for review by a health care professional.

18 Claims, 2 Drawing Sheets

(52) U.S. Cl.
CPC ........ *A61B 6/502* (2013.01); *G06T 2211/408* (2013.01); *G06T 2211/436* (2013.01)

(56) References Cited

U.S. PATENT DOCUMENTS

| | | | | |
|---|---|---|---|---|
| 6,795,068 | B1* | 9/2004 | Marks | G06F 3/0304 345/419 |
| 7,693,318 | B1* | 4/2010 | Stalling | G06T 11/006 128/922 |
| 7,778,392 | B1* | 8/2010 | Berman | A61B 6/032 378/210 |
| 8,189,002 | B1* | 5/2012 | Westerhoff | G06T 15/005 345/419 |
| 2002/0122537 | A1* | 9/2002 | Yoshimura | A61B 6/0478 378/208 |
| 2003/0142787 | A1* | 7/2003 | Jabri | A61B 6/4233 378/98.12 |
| 2004/0086076 | A1* | 5/2004 | Nagaoka | A61B 6/032 378/4 |
| 2005/0084060 | A1* | 4/2005 | Seppi | A61B 6/032 378/5 |
| 2005/0094759 | A1* | 5/2005 | Hagiwara | A61B 6/032 378/4 |
| 2006/0269114 | A1* | 11/2006 | Metz | G06T 11/005 382/131 |
| 2007/0036263 | A1* | 2/2007 | Nishide | A61B 6/032 378/4 |
| 2007/0206724 | A1* | 9/2007 | Sakaguchi | A61B 6/481 378/62 |
| 2008/0082002 | A1* | 4/2008 | Wilson | A61B 5/02007 600/483 |
| 2008/0232540 | A1* | 9/2008 | Yoshimura | A61B 6/032 378/4 |
| 2008/0240510 | A1* | 10/2008 | Dale | G06K 9/00 382/108 |
| 2009/0147919 | A1* | 6/2009 | Goto | A61B 6/032 378/86 |
| 2009/0232272 | A1* | 9/2009 | Tsujii | A61B 6/00 378/16 |
| 2010/0111389 | A1* | 5/2010 | Strobel | A61B 6/12 382/131 |
| 2010/0290585 | A1* | 11/2010 | Eliasson | A61B 6/025 378/37 |
| 2012/0051500 | A1* | 3/2012 | Johansson | A61B 6/025 378/22 |
| 2012/0134464 | A1* | 5/2012 | Hoernig | A61B 6/025 378/22 |
| 2012/0148133 | A1* | 6/2012 | Chen | A61B 6/032 382/131 |
| 2013/0272494 | A1 | 10/2013 | DeFreitas et al. | |
| 2014/0072096 | A1 | 3/2014 | Hoernig | |
| 2015/0335305 | A1* | 11/2015 | Moon | A61B 6/461 378/98.5 |

\* cited by examiner

METHOD AND SYSTEM FOR OBTAINING LOW DOSE TOMOSYNTHESIS AND MATERIAL DECOMPOSITION IMAGES

BACKGROUND

X-ray imaging systems have become a valuable tool in medical applications such as for the diagnosis of many diseases. As standard screening for breast cancer mammography 2-dimensional (2D) x-ray images are commonly used that record the images on a photographic film. Since mammograms take only 2D images across the entire breast tissue superimposition may occur. Thus, lesions may be masked by the tissue above or underneath, or normal structures may mimic a lesion. Since the accuracy of 2D mammograms are limited, especially in dense breasts, the addition of functional information can improve diagnostic accuracy.

For functional information, Contrast Enhanced Spectral Mammography (CESM) can be provided, which is a special type of mammogram that is performed after injecting x-ray intravascular contrast such as iodine. CESM involves the acquisition of x-ray images using multiple-energy radiation sequences. That is to say a number of images of the same object are acquired that reveal the x-ray transmittance of the object, such as a patient's breast, for differing x-ray spectra. In dual energy imaging, two images of the same object are acquired sequentially under different x-ray beam conditions as follows: One image at a low energy (LE) level, which is similar to a conventional 2D-mammographic image, and a second image at a high energy (HE) level, which is used for optimally detecting the contrast agent to indicate vascular information from angiogenesis. The image data at the different energy levels may be used to obtain energy selective images or in order to get the material decomposition of the object of interest. Hence, the data processing methods that make use of dual energy data may also be referred to as decomposition technique to obtain material decomposition images. This method enhances the contrast between different tissues or materials and especially when contrast material is used. After acquiring two images at different x-ray energies, the LE image and HE image are combined or subtracted to generate a functional image, which cancels the image contrast of adipose and glandular breast tissues and at the same time highlights areas with increased blood supply. Since breast cancer typically has a larger blood supply than normal tissue, the highlighted areas on the material decomposition images may aid in detection, diagnosis and staging of breast lesions.

The contrast enhanced spectral mammography (CESM) for 2D functional information in material decomposition images using the dual energy technique requires additional radiation exposure compared to a known 2D mammogram. The dose for dual energy CESM can be up to 1.4 times the dose of a known 2D mammogram. If a radiologist wants to further benefit from 3D morphological information along with a 2D functional image, he can perform besides the dual energy CESM imaging a digital tomosynthesis acquisition. In digital breast tomosynthesis (DBT) the volume information of an object of interest is usually derived from a series of images at various angles, wherein each so-called projection image is taken at substantially lower x-ray dose than the known 2D mammogram. However, if digital tomosynthesis is implemented besides 2D CESM the total dose delivered to the object increases up to 2.2 to 2.4 times the 2D regular mammography dose. Since the relatively high radiation dose limits the implementation of such combo techniques, there is the need to provide an imaging technique that performs both tomosynthesis and 2D CESM for lower radiation doses.

SUMMARY OF THE INVENTION

In one aspect, the present disclosure is directed to a method for obtaining tomosynthesis and material decomposition images of an object of interest using a system comprising an x-ray source facing a detector. The method comprises generating a 2D material decomposition image of an object of interest comprising a material from at least two sets or modes of acquisitions, wherein each set is performed at a different energy spectrum and comprises at least one projection image or a plurality of projection images acquired at different x-ray source angulation positions, and wherein the 2D material decomposition image can be generated for a predetermined orientation selected from one of said different x-ray source angulation positions or from a virtual orientation.

In this way a synthetic 2D material decomposition image enhancing the high-density contrast material can be generated. The contrast agent may be iodine or silver or any other suited material injected into the blood flow before the imaging system is operated. At the considered x-ray beam energies, they attenuate the x-rays more than body tissues. In the contrast enhanced image the radiologist can better localize cancerous cells and tumors.

In another aspect, the present disclosure is directed to a method for obtaining tomosynthesis and contrast-enhanced images of an object of interest using a system comprising an x-ray source facing a detector. The method comprises acquiring a plurality of 2D projection images of the object of interest in a plurality of orientations using x-ray radiation having a first energy spectrum, when the system is operating in a first mode; generating from the plurality of 2D projection images tomosynthesis data comprising a plurality of 3D volume portion images of the object of interest; and acquiring 2D image of the object of interest in a predetermined orientation using x-ray radiation having a second energy spectrum, when the system is operating in a second mode. Further, the method comprises generating a synthetic 2D image from the tomosynthesis data of the first energy spectrum in the predetermined orientation; generating a 2D material decomposition image by combining the synthetic 2D image of the first energy spectrum and the 2D image acquired at a second energy spectrum; and displaying at least one of the plurality of 3D volume portion images and/or the 2D contrast enhanced image.

The method is not restricted to the above given order. For example, the first mode can be performed after performing the second mode. According to an embodiment of the disclosure the synthetic 2D image is computed for a predetermined orientation based on the tomosynthesis data comprising images acquired in the first mode. In this case, the generation of the synthetic 2D image can only performed after the acquisition steps have been performed in both modes.

In yet another aspect, the present disclosure is directed to a method for obtaining tomosynthesis and material decomposition images of an object of interest using a system comprising an x-ray source facing a detector. The method comprises acquiring a plurality of 2D projection images of the object of interest in a plurality of orientations using x-ray radiation having a first energy spectrum, when the system is operating in a first mode; generating from the plurality of 2D projection images tomosynthesis data comprising a plurality of 3D volume portion images of the object of interest; and acquiring a 2D image of the object of interest in a predetermined orientation using x-ray radiation having a second energy spectrum, when the system is operating in a second mode. Further, the method comprises generating a synthetic 2D image from the tomosynthesis data of the first energy spectrum in the predetermined orientation; generating a 3D material decomposition volume by combining at least one of the volume portions of the first energy spectrum and the 2D image acquired at a second energy spectrum; and displaying at least one of the plurality of 3D material decomposition volume portion.

Before operating the imaging system, a contrast medium or agent is preferably intravenously introduced in the object of interest such as a patient in order to enable the generation of a material decomposition image. Accordingly, one material to be decomposed is the contrast medium. The second energy spectrum of the second mode is preferably selected using an energy window bracketing of the absorption peak of the contrast agent in order to achieve optimally contrast enhanced images, which is for example obtained with high energy (HE) x-ray spectrum if iodine is used as contrast agent.

According to another embodiment of the disclosure, the contrast medium is introduced in the object of interest, such as a patient's breast, at a time period before the system is operating in the first mode and second mode, in order to allow the contrast medium to distribute from the contrast injection port over the blood to the female breast before the x-ray examination starts. In this way both acquisition modes, i.e. tomosynthesis and material decomposition image acquisition, can be performed in a single examination without time delay between the two modes. In this way the same position and compression of the object of interest such as a female breast can be used for examination. Using one single examination for both modes allows for a better registration between LE (morphological) and recombined (functional) image information.

In yet another aspect, the present disclosure is directed to a method for obtaining material decomposition images, the method further comprising:
  recombining the at least two sets of projection images to obtain a series of projection images representing the material; and
  reconstructing the resulting recombined projections to generate a volume of the material, which is reprojected to generate a 2D material decomposition image.

In yet another aspect, the present disclosure is directed to a method, wherein each of the at least two sets of projection images are reconstructed to obtain 3D volumes, the method comprising recombining said 3D volumes to obtain a 3D volume representing the material and said 3D volume is then reprojected to generate a synthetic 2D material decomposition image.

According to another embodiment of the disclosure the first energy spectrum of the tomosynthesis acquisition is corresponding to a low energy, which is lower than the second energy spectrum comprising a high energy level (HE). This low dose tomosynthesis image not only allows/provides morphological information for diagnosis, but is also used for computing the synthetic 2D image of the first energy spectrum, which may in the following also be called low energy (LE)-2D image.

According to yet another embodiment of the disclosure, a total dose after image acquisition in the first and second mode is achieved, which dose is lower than the sum of the dose of a tomosynthesis acquisition and the dose of a dual energy 2D contrast enhanced spectral mammography. Preferably, the total dose according to an embodiment of the invention is similar or about equal to the dose of a dual energy 2D contrast enhanced spectral mammography (CESM).

According to yet another embodiment of the disclosure, the method step of displaying further comprises displaying the synthetic 2D image and/or on demand of a user switching between the tomosynthesis images, the synthetic 2D image and the 2D material decomposition image. In this way the workflow for the user and the analysis of object characteristics is optimized. For further user comfort the switching between the different images is provided using a progressive fading functionality. Moreover, object characteristics as vascular information based on the 2D material decomposition image can be added on demand as highlighted and/or colored region to the 2D synthetic image or the volume portion.

According to another embodiment of the disclosure the generation of the synthetic 2D image of the first energy spectrum provides a navigation map linking each pixel of the synthetic 2D image to the height of a 3D volume portion. In another aspect, the present disclosure is directed to a method, wherein clicking on a pixel of the 2D material decomposition image allows displaying the 3D volume portion of height provided by the navigation map in that pixel. According to another embodiment of the disclosure the navigation map is merged with the 2D material decomposition image preferably by using color information.

In another aspect, the present disclosure is directed to a computer program product, which computer program product comprises program instructions for carrying out each of the method steps of the disclosure, when said product is executed on a computer.

In another aspect, the present disclosure is directed to a computer readable medium storing program instructions, which, when executed by a processor of a computer cause the computer to perform each of the method steps of the disclosure.

In another aspect, the present disclosure is directed to a system for obtaining tomosynthesis and material decomposition images of an object of interest using a system comprising an x-ray source facing a detector, configured to
  generate a 2D material decomposition image of an object of interest from at least two sets of acquisitions, wherein each set is performed at a different energy spectrum and comprises at least one projection image or a plurality of projection images acquired at different x-ray source angulation positions;
  wherein the 2D material decomposition image can be generated for a predetermined orientation selected from one of said different x-ray source angulation positions or from a virtual orientation.

In another aspect, the present disclosure is directed to a system for obtaining images of an object of interest, such as a patient's breast, the system comprising:
  an imaging system comprising an x-ray source and a detector configured to acquire a plurality of 2D projection images of the object of interest in a first mode and to acquire a 2D image of the object of interest using x-ray radiation having a second energy spectrum in a predetermined orientation in a second mode;
  a processor configured to generate a plurality of 3D volume portions of the object of interest from the plurality of 2D projection images and to generate a 2D contrast enhanced image by combining a synthetic 2D image of the first energy spectrum and the 2D image acquired at a second energy spectrum; and a display unit for displaying the at least one of the 3D volume portion images and/or a 2D contrast enhanced image.

At least one of the above embodiments provides one or more solutions to the problems and disadvantages of the background art. One advantage that may be realized in the practice of all or some embodiments of the described methods and systems is that two modes can be provided while maintaining the total radiation exposure equal or similar to the dose of only one mode. Other technical advantages of the present disclosure will be readily apparent to one skilled in the art from the following description and claims. Various embodiments of the present application obtain only a subset of the advantages set forth. No single advantage is critical to the embodiments. Any claimed embodiment may be technically combined with any other claimed embodiments.

BRIEF DESCRIPTION OF THE DRAWINGS

The accompanying drawings illustrate exemplary embodiments of the disclosure and serve to explain, by way of example, the principles of the disclosure.

DETAILED DESCRIPTION

Figure 1:
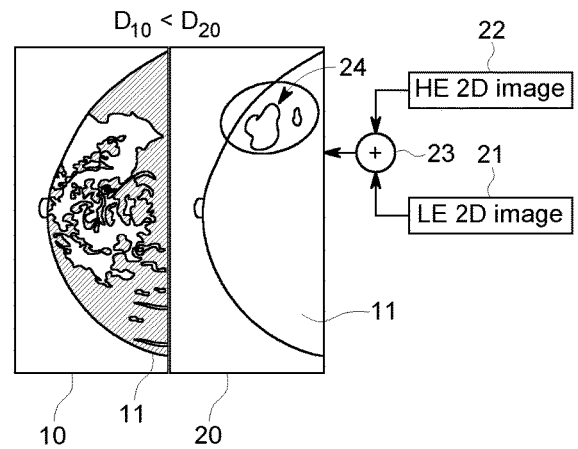
FIG. 1 shows a known 2D mammography image besides material decomposition image retrieved from a dual energy acquisition.

FIG. 1 shows a known 2D mammography image 10 besides a material decomposition image 20 retrieved from a contrast enhanced spectral mammography (CESM). Both images 10 and 20 have been acquired by using x-ray radiation sequences and show the same portion of a female breast 11. The images have been acquired in two distinct examinations. One difference between the examinations is that for the material decomposition image 20, first a contrast agent, such as an iodine based medium is introduced via an injection (not shown in FIG. 1). Then 2D images of the breast are acquired using two different x-ray energy spectra, resulting in a low energy 2D image 21 and a high energy 2D image. These two images 21 and 22 are digitally combined in step 23. The resulting contrast enhanced material decomposition image 20 shows a brighter area 24 of increased blood supply indicating angiogenesis, which may have been stimulated by cancer cells. White areas corresponding to dense breast tissue as imaged in the known 2D mammogram 10 are hided in the material decomposition image 20.

One disadvantage of the combo technique shown in FIG. 1 is that it exposes the patient to an increased radiation dose compared to known x-ray 2D mammography. Thus, there is the need to keep the dose for a female patient as low as possible. FIG. 1 shows a known 2D mammography image 10 which is obtained by a separate exam corresponding to an exposure of an x-radiation resulting in a dose $D_{10}$. Further, the acquisition of the contrast enhanced material decomposition image 20 requires a dual energy exposure, resulting in a higher dose $D_{20}$ in comparison to dose $D_{10}$ typically used for known 2D mammograms. Using both imaging techniques as a combo the total dose is at least the aggregate of $D_{10}$ and $D_{20}$. Such relatively high doses need to be avoided. Further there is the need to further provide reliable morphological information.

Figure 2:
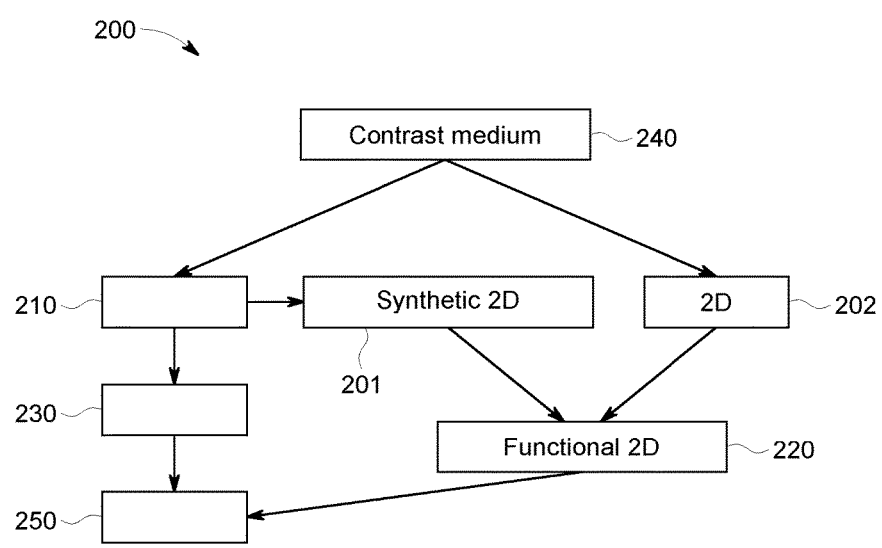
FIG. 2 is a diagrammatic flow chart of a method for generating both tomosynthesis images and a 2D material decomposition image according to an exemplary embodiment of the disclosure.

FIG. 2 shows a dual mode x-ray examination 200 of a contrast-enhanced object of interest. A 2D material decomposition image of said contrast-enhanced object of interest can be generated from at least two modes or sets of acquisitions, wherein each set is performed at a different energy spectrum and comprises at least one projection image or a plurality of projection images acquired at different x-ray source angulation positions. The first mode comprises the acquisition and generation of tomosynthesis data (method steps 210 and 230), which can provide morphological information. Further, there is a second mode to obtain functional information comprising the acquisition and generation of a contrast enhanced 2D material decomposition image (see method steps 201, 202 and 220). Before starting both modes, in a first step 240, contrast medium, for example iodine, is injected into a blood vessel of the patient. After the injection 240, time is allotted to allow the contrast medium to reach a detectable concentration in the patient's breast.

After compression of the contrast enhanced patient's breast, two sets or modes of acquisitions can be started. The tomosynthesis mode comprises a first method step 210 to acquire a plurality of 2D projection images of the object of interest in a plurality of orientations using x-ray radiation having a first energy spectrum. In a second method step 230, at least one 3D volume of the object of interest from the plurality of 2D projection images is generated. In a third method step 250, the at least one generated 3D volume of the object of interest or at least one portion thereof is displayed. In one embodiment, by displaying in method step 250 a plurality of 3D volume portions, morphological information can be provided which can be reviewed and analyzed by the health professional in a workstation.

The second mode (see method steps 201, 202 and 220) is applied for obtaining a contrast-enhanced 2D material decomposition image in order to further provide functional information for diagnosis. The 2D material decomposition image can be generated for a predetermined orientation selected from one of the different x-ray source angulation positions or from a virtual orientation. The method in the second mode comprises at least:

acquiring in step 202 a 2D image of the object of interest in a predetermined orientation using x-ray radiation having a second energy spectrum;

generating in step 201 a synthetic 2D image in the predetermined orientation in relation to the first energy spectrum, wherein said synthetic 2D image can be generated with the aid of the acquired tomosynthesis data acquired in step 210; and generating in step 220 a 2D material decomposition image by combining the synthetic 2D image 201 of the first energy spectrum and the 2D image 202 acquired at a second energy spectrum.

By generating a synthetic 2D image less x-ray radiation is needed for generating the functional 2D material decomposition image 220. Hence, one difference of the contrast enhanced acquisition technique according to the second mode of method 200 is that only one radiation exposure at a predetermined spectrum is performed compared to the dual energy technique shown in FIG. 1, which performs two radiation sequences for obtaining a low energy (21) and a high energy (22) image, respectively. Thus, the dose necessary for generating the functional 2D image 220 can be reduced compared to the dose $D_{20}$, which is necessary for the dual energy material decomposition image 20 as shown in FIG. 1. According to the embodiments of the invention described in this disclosure, less radiation exposure is required for obtaining the clinically relevant functional information. In total, the dose of the dual mode method 200 providing both tomosynthesis images 230 and contrast enhanced material decomposition images 220 is similar or about equal to the dose $D_{20}$ of a contrast enhanced spectral mammography (CESM).

In method step 250, various display modes are available to a user or healthcare personnel for diagnosis. Besides the 3D volume portions 230, functional information of a contrast enhanced spectral 2D material decomposition mammogram 220 can also be displayed. A reviewer as a healthcare professional or radiologist may either switch between the morphological or functional image or look at the images simultaneously. There is another advantageous display mode possible, if in method step 201 (generating a synthetic 2D image) a navigation map is generated, which links each pixel of the synthetic 2D image to the height of a 3D volume portion. The corresponding display mode can enable, that clicking on a pixel of the 2D material decomposition image or the synthetic 2D image allows displaying the 3D volume portion of height provided by the navigation map in that pixel.

Figure 3:
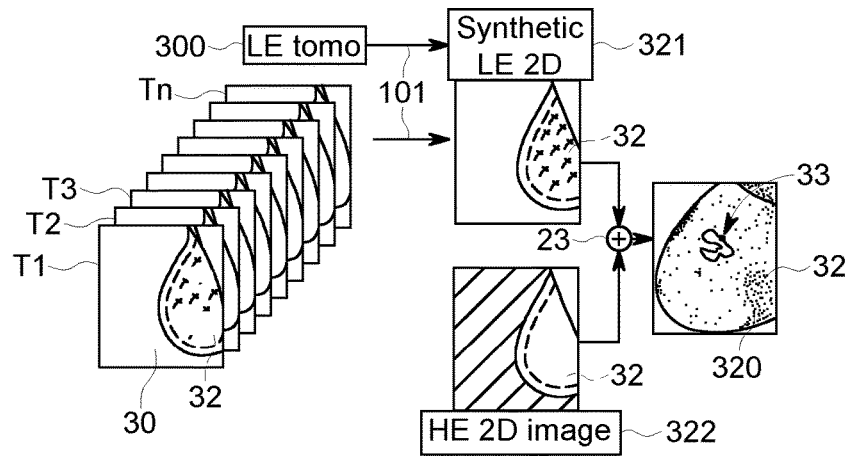
FIG. 3 is diagrammatic illustration of a work and data flow for reviewing images of an object of interest according to another exemplary embodiment of the disclosure.

FIG. 3 shows a diagrammatic illustration of a work and data flow for reviewing morphological and functional images of an object of interest being a patient's breast 32. As in FIG. 2 the method comprises two modes. The data acquisition in the tomosynthesis mode 300 is performed at a low dose using a first energy spectrum (low energy LE tomo 300). This low energy tomosynthesis 300 is preferably less than or equal to the dose $D_{10}$ of a known 2D mammogram. The dose for acquiring the plurality of volume portions Tn depends on the number of projection images, the limitation of the angular range and other imaging system settings such as the amount radiation energy used. Hence, the system conditions for tomosynthesis are set such that a low energy tomosynthesis 300 can be performed and at the same time high quality images can be achieved.

Each of the plurality of volume portions T1, T2, T3 . . . Tn, which have been acquired by the low energy dose tomosynthesis 300, can be reviewed by a healthcare professional or radiologist on demand. FIG. 3 shows schematically a display 30 of a 3D volume portion T1, which may also be called a tomo plane. This set of 3D volume portions Tn, which are generated from a plurality of 2D projection images, are relatively thin slices having a thickness of about 1 mm. In this way tissue superimposition as encountered in a known 2D mammogram (see white areas in image 10 in FIG. 1) may be excluded and a healthcare professional may, with aid of the 3D volume portions Tn, precisely analyze clinical relevant structures as microcalcifications having a size ranging from 100 µm to 500 µm. In this way morphological information can optimally be assessed by the healthcare professional.

The tomosynthesis low energy projection images can advantageously be used in order to generate a synthetic 2D image for a predetermined orientation corresponding to a low energy level or first energy spectrum. In FIG. 3 such a low energy 2D image 321 is computed in step 101 and may optionally be displayed in step 321. Moreover the second mode of obtaining contrast enhanced spectral mammograms further comprises at least the following steps:

acquiring 2D image of the object of interest in a predetermined orientation using x-ray radiation having a second energy spectrum, wherein the second energy spectrum has a high energy level resulting in the shown HE 2D image 322;

generating a 2D material decomposition image 320 by combining the synthetic 2D image of the first energy spectrum and the 2D image acquired at the high energy level in step 23; and displaying the 2D material decomposition image of the patient's breast 32 showing contrast enhanced areas 33 indicating increased blood supply.

According to another embodiment, optionally a 3D material decomposition volume by combining at least one of the volume portions of the first energy spectrum and the 2D image acquired at a second energy spectrum can be generated. At least one of the plurality of 3D material decomposition volume portion can be displayed for review.

For displaying the different images 30, 321 and 320, a switching mode may be provided to toggle between them. Thus the user may select to see a display of at least one 3D volume portion, a set of 3D volume portions Tn, a synthetic 2D image 321 or a 2D material decomposition image 320. Further, to improve image analysis for a health care professional, progressive-fading functionality between the different displays may be provided. And image analysis is even further eased if on demand object characteristics, such as vascular information based on the combined 2D contrast enhanced material decomposition image(s), are added onto the synthetic 2D image 321 or onto a 3D volume portion in the form of highlighted and/or colored regions.

By using the methods according to the present disclosure, the benefits of 3D tomosynthesis morphological information (see display 30 and Tn in FIG. 3) are provided along with the benefits of 2D functional imaging (320). In the embodiments, wherein only one 2D image in a predetermined orientation is acquired in the CESM acquisition mode and a plurality of projection images in the tomosynthesis mode a patient is exposed to lower radiation doses in comparison to the radiation doses associated with the traditional combined application of these two techniques.

Further, there are additional technical advantages for example, x-ray source usage is decreased, which reduces system wear and increases throughput. Moreover, the acquisition sequence can be simplified for both the healthcare professional and patient. Since tomosynthesis based images and material decomposition/CESM images have proven clinical value, the healthcare professional has a valuable base from which to make accurate diagnosis. Moreover, the method according to the present disclosure is especially advantageous for patients with dense breasts, wherein both morphological and functional information are needed.

In yet another embodiment of the method, wherein two sets of projection images are acquired at a different energy spectrum and each set comprises a plurality of projection images, the images for material decomposition images are obtained as follows:

recombining the at least two sets of projection images to obtain a series of projection images representing the material; and reconstructing the resulting recombined projections to generate a volume of the material, which is reprojected to generate a 2D material decomposition image.

As an alternative to the above method the reconstruction step can be performed earlier: First each of the at least two sets of projection images are reconstructed to obtain 3D volumes. Then follows the step of recombining said 3D volumes to obtain a 3D volume representing the material. Said 3D volume is then reprojected to generate a synthetic 2D material decomposition image.

Figure 4:
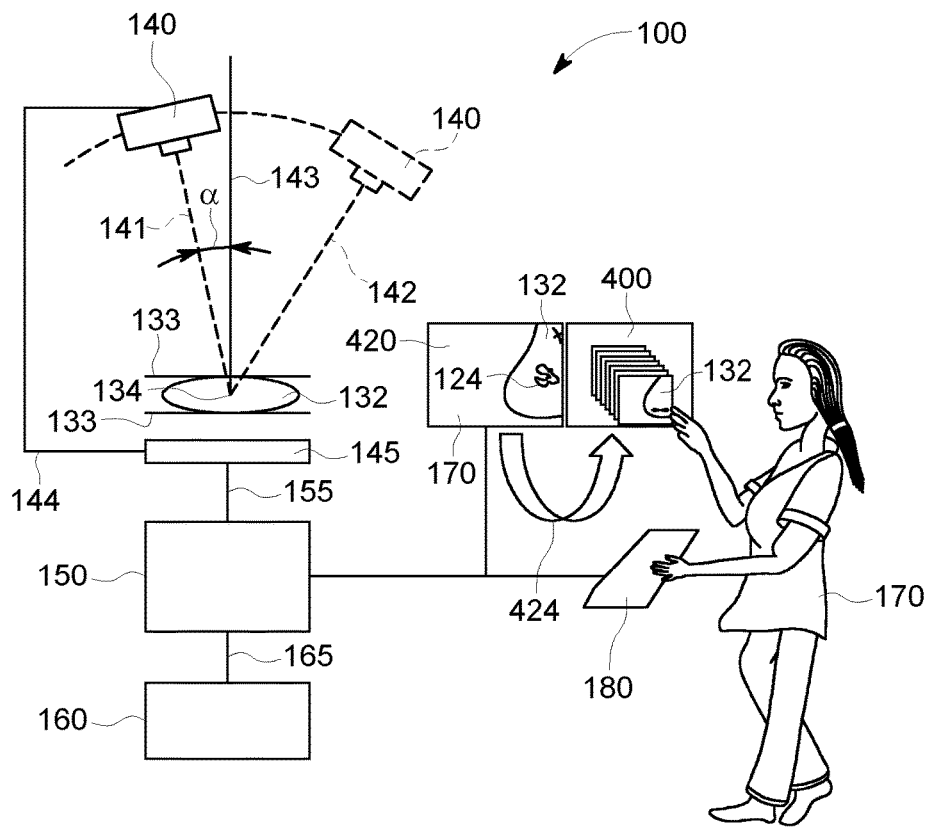
FIG. 4 shows a diagrammatic illustration of a system for obtaining images according to another exemplary embodiment of the disclosure.

FIG. 4 shows a system for obtaining tomosynthesis and material decomposition images of an object of interest according to an embodiment of the disclosure, wherein the system 130 comprises an x-ray beam source 140 facing the detector 145. The x-ray beam source 140 and the detector 145 are connected by an arm 144. Between the detector 145 and the source 140 an object of interest 132, such as a patient's breast, can be placed.

When acquiring a first set of images in a tomosynthesis mode (first mode) the system 100 moves the x-ray source 140 in an arc above a single detector 145. Alternatively, the source 140 may be held stationary, while one or more detectors 145 are moved or both the source 140 and the detector 145 move. Regardless of the acquisition geometry used, multiple different views of the breast tissue can be acquired via the at least one x-ray source 140. Each of the multiple different views generally corresponds to a different position of the x-ray source 140 and the image receiver in relation to the object of interest 132 resulting in different orientations. For acquisition in the second mode only, one predetermined orientation is selected which may, for example, be the zero orientation 143 or alternatively any other orientation 141 suited for optimal image acquisition or for comparison with former images.

The object of interest 132, such as a breast, is compressed by the compression paddles 133 for the duration of the examination. Before the examination, the contrast agent is injected. The compression starts after a time interval ensuring that the contrast medium has effectively been distributed in the breast 132. The actual compression time can be reduced to the time needed for data acquisition in the two modes. The detector 145 and the x-ray source 140 constitute the acquisition unit, which is connected via a data acquisition line 155 to a processor 150. The processor 150 comprises a memory unit 160, which may be connected via an archive line 165, and performs the generation of 3D volume portions 400, as well as the 2D synthetic image and the combined contrast enhanced image 420. These generating or processing steps may partially be performed simultaneously by using a plurality of sub processing units.

A user, such as a healthcare professional 181, may input control signals via the user interface 180. Such signals are transferred from the user interface to the processing unit 150 via the signal line 185. The method and system according to the disclosure enables the user to obtain access to one or more displays or display modes, respectively. First, the user may review the obtained image of the object of interest 132 on a display unit 170 showing the display 400 of the 2D material decomposition image for functional information, as illustrated by the highlighted object 124. Second, high quality images for morphological information are shown in the tomosynthesis display 420. As an alternative to viewing both displays simultaneously, only one display may be provided, wherein the user may switch on demand between the distinct image displays 400 and 420. Further, 3D volume information can also be retrieved from optionally generated 3D material decomposition images. By further using color coding or other highlighting techniques, a radiologist is able to better identify all the clinical signs relevant to breast screening. For example, clicking on a pixel of the 2D material decomposition image or the 2D synthetic image enables a displaying of the 3D volume portion of height provided by a navigation map in that pixel. Said navigation map may be provided from the synthetic 2D image of the first energy spectrum and links each pixel of the synthetic 2D image to the height of a 3D volume portion.

If the healthcare professional is familiar with 2D standard mammograms, there is further the possibility of displaying synthetic 2D images of the entire volume of the breast. These synthetic 2D images may also be compared with 2D mammograms, which have been archived in a medical record from former examinations. For better diagnosis, information of the functional image 420 may be superimposed in/on the synthetic 2D image.

According to another embodiment of the disclosure, the user can archive in a memory unit 160 one or more from the images, which have been generated according to a method of the present disclosure. The memory unit 150 can be integral or separate from the one or more processors 150. The memory unit 160 allows storage of data such as the 3D volume portion images, synthetic 2D images, 2D material decomposition images and/or 3D material decomposition images. In general the memory unit 160 may comprise a computer-readable medium for example a hard disk or a CD-ROM, diskette, a ROM/RAM memory, DVD, a digital source such as a network or the Internet or any other suitable means. The processor 150 is configured to execute program instructions stored in the memory unit 160, which cause the computer to perform the methods of the disclosure. One technical effect of performing the method according to the embodiments of the disclosure is to reduce examination time and thus throughput of the x-ray source, such as an x-ray tube.

This description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

What is claimed is:

1. A Method for obtaining tomosynthesis and material decomposition images of an object of interest using a system comprising an x-ray source facing a detector, the method comprising:

acquiring a plurality of 2D projection images of the object of interest in a plurality of orientations based on different x-ray source angulation positions using x-ray radiation having a first energy spectrum, when the system is operating in a first mode;

generating from the plurality of 2D projection images tomosynthesis data comprising a plurality of 3D volume portion images of the object of interest;

acquiring a 2D image of the object of interest in a predetermined orientation using X-ray radiation having a second energy spectrum, when the system is operating in a second mode;

generating a synthetic 2D image from the tomosynthesis data of the first energy spectrum in a predetermined orientation; and generating a 2D material decomposition image of the object of interest from the two sets of acquisitions, each performed at a different energy spectrum, by combining the synthetic 2D image of the first energy spectrum and the 2D image acquired at the second energy spectrum, wherein the material decomposition image can be generated for a predetermined orientation selected from one of said different x-ray source angulation positions or from a virtual orientation.

2. The method according to claim 1, further comprising:
displaying at least one of the plurality of 3D volume portion images and/or the 2D material decomposition image.

3. The method according claim 1, further comprising providing a breast of a patient as an object, wherein a material is a contrast agent introduced in the patient's breast before the system is operating in the first and second mode.

4. The method according to claim 1, wherein the x-ray source angulation positions are the same, the method further comprising:
recombining the sets of projection images to obtain a series of projection images representing the material; and
reconstructing the resulting recombined projections to generate a 3D volume of the material, which is reprojected to generate a synthetic 2D material decomposition image.

5. The method according to claim 1, wherein each of the sets of projection images are reconstructed to obtain 3D volumes, the method further comprising; recombining said 3D volumes to obtain a 3D volume representing the material and said 3D volume is then reprojected to generate a synthetic 2D material decomposition image.

6. The method according to claim 1, further comprising performing the tomosynthesis acquisition at a first energy spectrum comprising a low energy (LE), which is lower than the high energy (HE) level of the second energy spectrum.

7. The method according to claim 1, wherein the total dose after image acquisitions in the first and second mode is about equal to the dose of a dual energy 2D contrast enhanced spectral mammography (CESM).

8. The method according to claim 2, wherein displaying further comprises switching between the display of 3D volume portions and the synthetic 2D image and the 2D material decomposition image.

9. The method according to claim 8, wherein a user actuated switching between the display of 3D volume portions or synthetic 2D image and the 2D material decomposition image is provided using a progressive fading functionality.

10. The method according to claim 1, wherein the generation of a synthetic 2D image provides a navigation map linking each pixel of the synthetic 2D image to the height of a 3D volume portion.

11. The method according to claim 10, wherein clicking on a pixel of the 2D material decomposition image or the synthetic 2D image allows displaying the 3D volume portion of height provided by the navigation map in that pixel.

12. The method according to claim 10, wherein the navigation map is merged with the 2D material decomposition image preferably by using color information.

13. The method according to claim 1, further comprising displaying the synthetic 2D image, wherein object characteristics such as vascular information based on the combined 2D material decomposition image are added on demand as highlighted and/or colored region to the synthetic 2D image.

14. The method according to claim 1, further comprising displaying a volume portion, wherein object characteristics such as vascular information based on the combined 2D material decomposition image are added on demand as highlighted and/or colored region to the volume portion.

15. A non-transitory computer readable medium storing program instructions, which, when executed by a computer cause the computer to perform the method according to claim 1.

16. A system for obtaining tomosynthesis and material decomposition images of an object of interest, the system comprising:
an x-ray source and an x-ray detector to acquire a plurality of 2D projection images of the object of interest in a plurality of orientations based on different x-ray source angulation positions using x-ray radiation having a first energy spectrum in a first mode and to acquire a 2D image of the object of interest using x-ray radiation having a second energy spectrum in a predetermined orientation in a second mode; and
a processor to generate a plurality of 3D volume portions of the object of interest from the plurality of 2D projection images and to generate a 2D material decomposition image by combining a synthetic 2D image of the first energy spectrum and the 2D image acquired at the second energy spectrum, wherein the 2D material decomposition image is generated for a predetermined orientation selected from one of the different x-ray source angulation positions or from a virtual orientation.

17. The system according to claim 16, further comprising:
a display unit for displaying at least one 3D volume portion of the object of interest and/or the 2D material decomposition image.

18. The system according to claim 16, wherein the object of interest is a patient's breast comprising as material an introduced contrast agent.

* * * * *